(12) United States Patent
Cui et al.

(10) Patent No.: US 11,517,195 B2
(45) Date of Patent: Dec. 6, 2022

(54) PANUM'S AREA MEASUREMENT METHOD, APPARATUS, AND WEARABLE DISPLAY DEVICE

(71) Applicant: CLOUDMINDS (SHENZHEN) ROBOTICS SYSTEMS CO., LTD., Guangdong (CN)

(72) Inventors: Huakun Cui, Guangdong (CN); Kai Wang, Guangdong (CN); Shiguo Lian, Guangdong (CN)

(73) Assignee: CLOUDMINDS ROBOTICS CO., LTD., Shanghai (CN)

( * ) Notice: Subject to any disclaimer, the term of this patent is extended or adjusted under 35 U.S.C. 154(b) by 394 days.

(21) Appl. No.: 16/809,194

(22) Filed: Mar. 4, 2020

(65) Prior Publication Data

US 2020/0260945 A1    Aug. 20, 2020

Related U.S. Application Data

(63) Continuation of application No. PCT/CN2017/100413, filed on Sep. 4, 2017.

(51) Int. Cl.
*A61B 3/08* (2006.01)
*A61B 3/00* (2006.01)
*A61B 5/11* (2006.01)

(52) U.S. Cl.
CPC ............ *A61B 3/08* (2013.01); *A61B 3/005* (2013.01); *A61B 3/0025* (2013.01); *A61B 3/0091* (2013.01); *A61B 5/1114* (2013.01)

(58) Field of Classification Search
CPC ......... A61B 3/08; A61B 3/0025; A61B 3/005; A61B 3/0091; A61B 5/1114;
(Continued)

(56) References Cited

U.S. PATENT DOCUMENTS

| | | | | |
|---|---|---|---|---|
| 2008/0252718 | A1* | 10/2008 | Provitola | G02B 30/52 348/E13.001 |
| 2012/0105609 | A1* | 5/2012 | Qi | A61B 3/08 348/54 |
| 2013/0083062 | A1* | 4/2013 | Geisner | G02B 27/017 345/633 |

FOREIGN PATENT DOCUMENTS

| | | | |
|---|---|---|---|
| CN | 102930550 A | * | 2/2013 |
| DE | 102015209484 A1 | * | 11/2016 |

* cited by examiner

*Primary Examiner* — Mohammed A Hasan

(57) ABSTRACT

A panum's area measurement method includes: projecting a first parallax image of a spatial object to the left eye of a user under test, and projecting a second parallax image of the spatial object to the right eye of the user under test, the first parallax image comprising a first homologous point and the second parallax image comprising a second homologous point; adjusting a horizontal parallax amount between the first homologous point and the second homologous point until the user under test observes the spatial object producing a ghost; acquiring a parallax amount parameter $\Delta n_e$; calculating a horizontal physical spacing $\Delta x$ between the first homologous point and the second homologous point based on the parallax amount parameter $\Delta n_e$; and calculating a panum's area range $(\mu_{in}, \mu_{out})$ of the user under test based on the horizontal physical spacing $\Delta x$.

14 Claims, 7 Drawing Sheets

(58) Field of Classification Search
CPC . G06T 2207/10012; G06T 2207/30041; G06T 2210/41; G06T 17/00; G06F 3/013
USPC ........................................................ 351/201
See application file for complete search history.

PANUM'S AREA MEASUREMENT METHOD, APPARATUS, AND WEARABLE DISPLAY DEVICE

CROSS-REFERENCE TO RELATED APPLICATIONS

This application is a continuation of International Application No. PCT/CN2017/100413 with an international filing date of Sep. 4, 2017, the entire contents of which are incorporated herein by reference.

TECHNICAL FIELD

The present application relates to the technical field of stereo-vision measurements, and in particular, relates to a panum's area measurement method and apparatus, and a wearable display device.

BACKGROUND

With the development of network technologies and machine vision and image recognition technologies, smart wearable display devices are more and more widely applied. For example, immersive virtual reality devices, augmented reality devices or even mobile terminals may be equipped with a wearable bracket to provide a realistic virtual environment and content for the users.

A single visionary image produced by visions of two eyes does not necessarily require that stimulations of light rays fall at absolute corresponding points of two retinas of the two eyes, and as a single image may be produced as long as the stimulations of the light rays fall within a specific range in the vicinity of the corresponding points. A monocular and small range formed in the vicinity of a corresponding point of a monocular retina is referred to as the panum's area. When the projection of an object is not within the panum's area, double images are formed. When the projection of the object is totally at corresponding points of two retinas, the object is perceived as a plane. If the projection of the object goes beyond the panum's area, the object is observed as double images; and if the projection of the object is neither completely at the corresponding points, nor goes beyond the panum's area, a three-dimensional vision is generated. Therefore, accurate measurement of the panum's area is significant for providing a comfortable stereo image for the wearable display device.

Stereo display technologies, for example, 3D movies, virtual reality (VR), augmented reality (AR) and the like, are mostly based on the binocular parallax principle, and thus provide three-dimensional stereo display full of senses of shock and immersion for users.

When users watch 3D screen, the positions of the points of an object on the screen observed by the left and right eyes may not coincide with each other, but are horizontally spaced. These two different points are imaged on the retinas, and then fused by the brain to a spatial point. This is the binocular parallax principle. The two points on the screen are generally called homologous points. A relative positional relationship between this pair of homologous points determines whether the brain fused spatial point seems to be distal from the watcher inside the screen or proximal to the watcher outside the screen. A horizontal distance between the homologous points is also referred to as a horizontal parallax. When the left eye sees a left side point in the homologous points and the right eye sees a right side point in the homologous points, a positive horizontal parallax is present, and in this case, the spatial point fused in the brain is outside the screen and the watcher and seems to enter the screen. When the left eye sees the right side point in the homologous points and the right eye sees the left side point in the homologous points, a negative horizontal parallax is present, and in this case, the spatial point fused in the brain is between the screen and the watcher and seems to protrude from the screen. The horizontal parallax is limited to a specific range. If the horizontal parallax increases to a specific degree or decreases to a specific degree, such increase or decrease may go beyond a fusion range of the human eyes. Consequently, a complete object may fail to be fused in the brain, and instead, a ghost is produced, which causes sickness for human eyes. When the horizontal parallax approaches zero, a relative sense of depth between landscapes may be weak, the stereo effect is not apparent, and the sense of immersion is not notable. When the horizontal parallax is zero, common two-dimensional display is provided. Generally, such range of positive and negative parallaxes is referred to as a panum's area in medicine.

However, in the prior art, there is no uniform standard for the measurement of the panum's area of the best stereo-vision of binocular. Under the same measurement method, a difference between a panum's area value measured by a user under test on device A and a panum's area value measured on device B is very large. How to provide a method and equipment that can be applied to different equipment and can accurately measure the panum's area has become an urgent problem.

Therefore, the tranditional panum's area measurement technology needs to be improved.

SUMMARY

An embodiment of the present application provides a panum's area measurement method. The method includes: projecting a first parallax image of a spatial object to the left eye of a user under test, and projecting a second parallax image of the spatial object to the right eye of the user under test, wherein the first parallax image includes a first homologous point and the second parallax image includes a second homologous point; adjusting a horizontal parallax amount between the first homologous point and the second homologous point until the user under test observes the spatial object producing a ghost; acquiring a parallax amount parameter $\Delta n_e$; calculating a horizontal physical spacing $\Delta x$ between the first homologous point and the second homologous point based on the parallax amount parameter $\Delta n_e$; and calculating a panum's area range ($\mu_{in}$, $\mu_{out}$) of the user under test based on the horizontal physical spacing $\Delta x$.

Another embodiment of the present application provides a wearable display device. The wearable display device includes a first display unit, a second display unit and an interaction end, wherein the wearable display device further includes an adjusting module and a measuring module that receive a signal from the interaction end; wherein the first display unit is configured to project a first parallax image of a spatial object to the left eye of a user under test, and the second display unit is configured to project a second parallax image of the spatial object to the right eye of the user under test, wherein the first parallax image includes a first homologous point and the second parallax image includes a second homologous point; the adjusting module is configured to adjust, under control of the interaction end, a horizontal parallax amount between the first homologous point and the second homologous point until the user under test observes the spatial object producing a ghost; and the measuring module is configured to acquiring a parallax amount parameter $\Delta n_e$, calculate a horizontal physical spacing $\Delta x$ between the first homologous point and the second homologous point based on the parallax amount parameter $\Delta n_e$, and calculate a panum's area range $(\mu_{in}, \mu_{out})$ of the user under test based on the horizontal physical spacing $\Delta x$.

Still another embodiment of the present application provides an electronic device. The electronic device includes: at least one processor; and a memory and a communication component that are communicably connected to the at least one processor; wherein the memory stores instructions executable by the at least one processor, wherein, the instructions, when being executed by the at least one processor, cause the at least one processor to establish a data channel by using the communication component, such that the at least one processor perform the method as described above.

BRIEF DESCRIPTION OF THE DRAWINGS

One or more embodiments are illustrated by way of example, and not by limitation, in the figures of the accompanying drawings, wherein components having the same reference numeral designations represent like components throughout. The drawings are not to scale, unless otherwise disclosed.

DETAILED DESCRIPTION

For clearer descriptions of the objectives, technical solutions, and advantages of the present application, the present application is further described with reference to specific embodiments and attached drawings. It should be understood that the specific embodiments described herein are only intended to explain the present application instead of limiting the present application.

Figure 1:
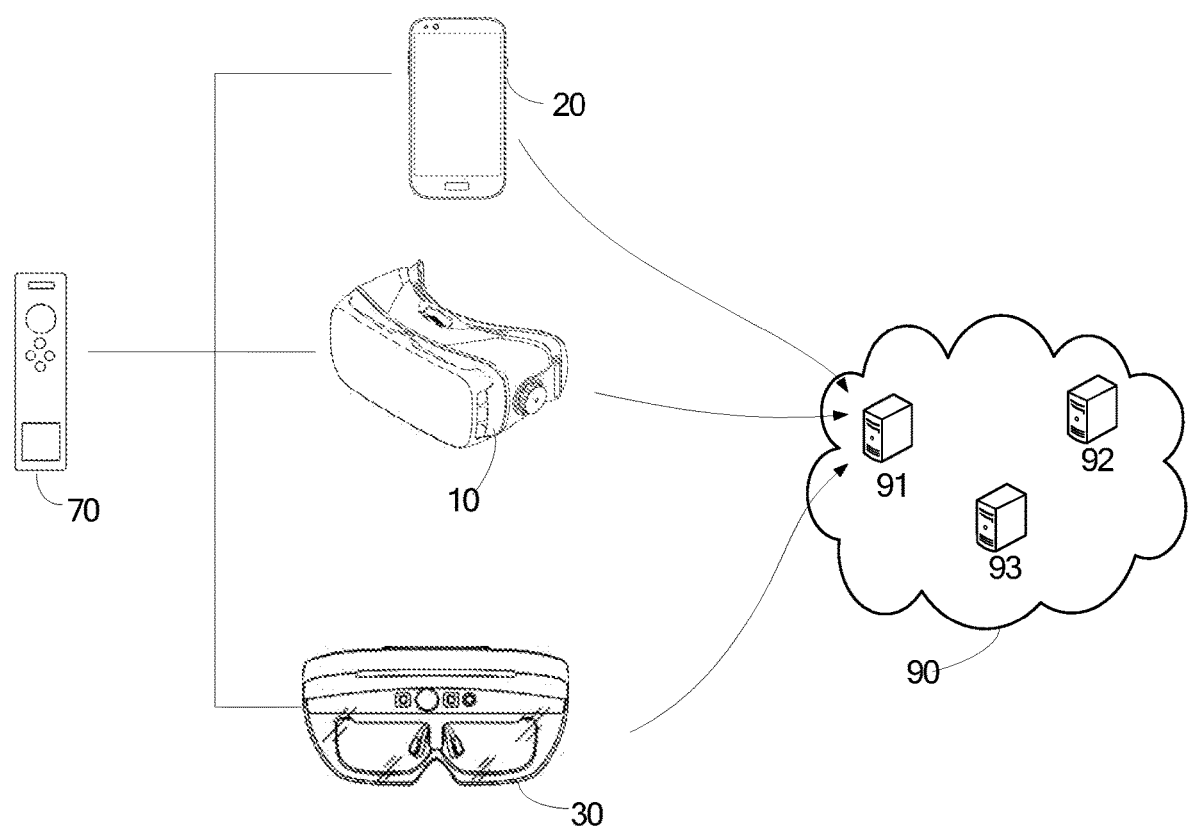
FIG. 1 is a schematic framework diagram of a panum's area measurement method according to an embodiment of the present application.

Referring to FIG. 1, a panum's area measurement apparatus according to the embodiments of the present application includes a wearable display device and an interaction end 70. In one embodiment, the wearable display device may be connected to an interaction cloud 90.

The interaction end 70 may be an interactive operation terminal configured for the wearable display device, for example, an interactive operation handle or an interactive operation glove or the like wearable interaction device. In another embodiment, the interaction end 70 may also be a head posture acquisition apparatus arranged in a wearable display helmet, wherein the head posture acquisition apparatus includes a gyroscope and an accelerometer configured to acquire a head rotation posture parameter of a user under test. For example, when the user under test rotates his or her head to the left (right), an instruction for decreasing (increasing) a horizontal physical spacing is generated; and when the user under test rotates his or her head to the right (left), an instruction for increasing (decreasing) the horizontal physical spacing is generated. The head posture acquisition apparatus adjusts a parallax amount parameter based on the head posture parameter of the user under test.

The wearable display device may be a virtual reality (VR) device 10. The wearable display device may also be an augmented reality (AR) device 30. The wearable display device may also be a mobile terminal 20. Each of the above exemplified wearable display devices may be wirelessly connected to the interaction end 70 and meanwhile wirelessly connected to an interactive cloud 90. The interactive cloud 90 is constructed by networking of a plurality of cloud servers 91 to 93.

The virtual reality device is a computer system that is capable of creating and providing a virtual three-dimensional world. The virtual reality device creates a three-dimensional virtual world reflecting in real time physical object changes and mutual interactions for users, and provides a vision for observing a virtual world and provides there-dimensional interactive operations for the user by auxiliary sensing equipment such as helmet displays, data gloves and the like, such that the user may directly participate in the interactive operations and explore changes and interactions of a simulated object in a virtual spatial environment. The virtual reality technology is a fruit of the computer technology, the sensing technology, the man-machine interface technology, the artificial intelligence technology and the like high technologies. Verisimilitude and real-time interaction provide solid supports for the system simulation technology, and meanwhile provide immersion, interaction and imagination. An augmented reality (AR) device further includes glasses by which the real world may be observed. By means of the glasses and a projected virtual three-dimensional image, the user may observe the real world while seeing the virtual three-dimensional world.

The wearable display device in this technical solution mainly include: a high-performance operation and processing unit, a three-dimensional display unit and an interaction end 40. The three-dimensional display unit includes two independent sets of sub display units, that is, a first display unit and a second display unit. These two sets of sub display units display two independent test images to the left eye and the right eye of the user. The high-performance operation and processing unit is configured to carry out real-time operation processing, and the interaction end 70 is configured to process input information of a user under test during the test process.

Therefore, the images presented by the wearable display device presents to two eyes of the user under test via the first display unit and the second display unit may all be finely adjusted, and thus a condition is provided for testing a panum's area of the user.

Panum's area measurement of the user is an important parameter for the user to recognize his or her three-dimensional vision of the eyes, and is also a basis for the wearable display device to provide comfortable three-dimensional content. A single-image small range formed in the vicinity of a corresponding point of a monocular retina is referred to as the panum's area. When the projection of an object is not within the panum's area, double images are formed. When the projection of the object is totally at corresponding points of two retinas, the object is perceived as a plane. If the projection of the object goes beyond the panum's area, the object is observed as double images; and if the projection of the object is neither at the corresponding points, nor goes beyond the panum's area, a stereo vision is generated. Therefore, accurate measurement of the panum's area is significant for providing a comfortable stereo image for the wearable display device.

Embodiment 1

This embodiment is related to a wearable display device 60 for use in panum's area measurement.

The wearable display device 60 displays, in a first display unit, a first parallax image that may be finely adjusted, and displays, in a second display unit, a second parallax image that may be finely adjusted. When a user under test wears a wearable helmet, the left and right eyes of the user respectively observe the first parallax image and the second parallax image, and adjust a horizontal physical spacing between the first parallax image and the second parallax image based on a clarity degree of an observed three-dimensional image, finds a critical position where a clear image is transformed from a blurry one, and finally predicts a panum's area range based on the measured horizontal physical spacing between the first parallax image and the second parallax image.

Figure 2:
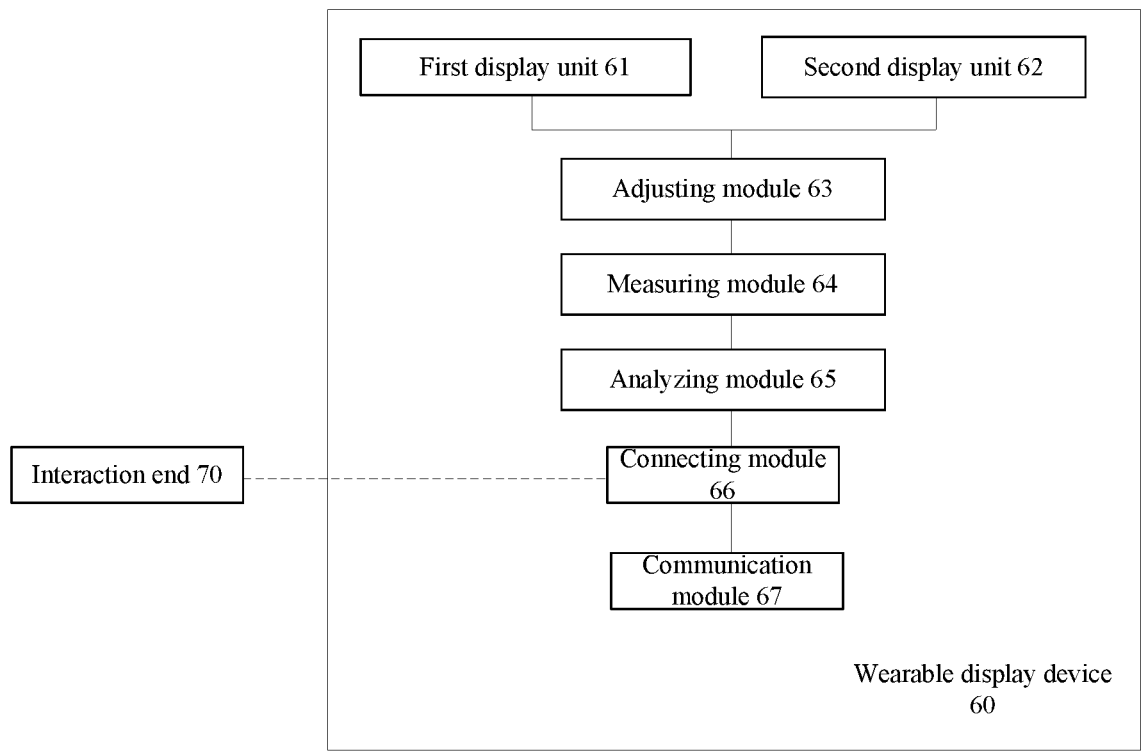
FIG. 2 is a schematic modular diagram of a panum's area measurement apparatus according to an embodiment of the present application.

Referring to FIG. 2, the wearable display device 60 includes a first display unit 61, a second display unit 62, an adjusting module 63, a measuring module 64, an analyzing module 65 and a connecting module 66.

The first display unit 61 and the second display unit 62 are left and right optical display systems on the wearable display device. The optical display systems correspond to the left eye and the right eye, and each optical display system includes a display screen and an imaging optical lens. The imaging optical lens may be a spherical lens, a non-spherical lens, a Fresnel's lens, a prism, a free curve half mirror, a waveguide grating or the like. The image on the display screen causes light rays to be incident to the corresponding eyes via the corresponding optical imaging lens, and to be imaged on the retinas.

The connecting module 66 is wirelessly connected to an interaction end 70 that is manually operated by the user. The interaction end 70 acquires an interaction instruction from the user under test, and sends the interaction instruction to the connecting module 66.

Figure 3:
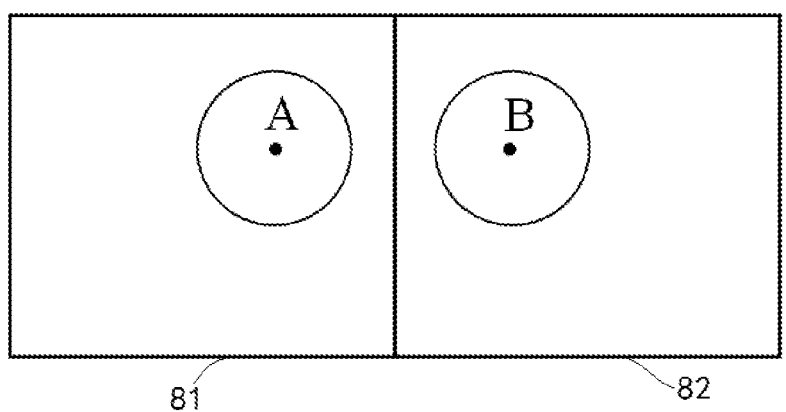
FIG. 3 is a schematic diagram of display content in a first display unit and a second display unit in the panum's area measurement apparatus according to an embodiment of the present application.

Referring to FIG. 3, for measurement of the panum's area range, two parallax images are projected to both eyes of the user under test by using the wearable display device. The first display unit 61 loads a first parallax image 81, and the second display unit 62 loads a second parallax image 82. The first parallax image 81 includes a first homologous point A, and the second parallax image 82 includes a second homologous point B.

The adjusting module 63 adjusts a horizontal parallax amount between the first homologous point A and the second homologous point B until the user under test observes the spatial object producing a ghost.

The measuring module 64 acquires a parallax amount parameter $\Delta n_e$, and calculate a horizontal physical spacing $\Delta x$ between the first homologous point and the second homologous point based on the parallax amount parameter $\Delta n_e$. The measuring module 64 further calculates a panum's area range $(\mu_{in}, \mu_{out})$ of the user under test based on the horizontal physical spacing $\Delta x$.

In FIG. 3, the first parallax image 81 and the second parallax image 82 respectively represent display content on a 2D display screen observed by left and right eyes by using the wearable display device. In FIG. 3, the display content is a spatial object, for example, a spatial sphere. Points A and B represent the first homologous point A and the second homologous point B, and two circles represent parallax images of a spatial object, for example, a basketball, on left and right display screens. According to this embodiment of the present application, by horizontally moving images on two display screens, the horizontal parallax amount between the first homologous point A and the second homologous point B on an image plane of a two-dimensional display screen is changed. For example, the horizontal parallax amount is adjusted from zero towards a positive parallax to determine an in-screen parallax amount parameter $\Delta n_{ein}$; and then the horizontal parallax amount is adjusted from zero towards a negative parallax to acquire an out-screen parallax amount parameter $\Delta n_{eout}$, and hence the panum's area range is determined. By this way, the panum's area range of the user under test may be accurately and standardly measured. The panum's area range may be used for detection and prevention of eye diseases. The panum's area range is of great significance for preparing more comfortable three-dimensional content.

In addition, the horizontal parallax amount may also be changed from a greater positive value towards a smaller value or even a negative value. Further, changes of the horizontal parallax amount within unit time.

In one embodiment, a panum's area measurement apparatus, for example, the wearable display device, may store the panum's area range of the user to a local memory upon measuring the panum's area range. Meanwhile, the panum's area measurement apparatus, for example, the wearable display device, further includes an analyzing module 65. The analyzing module 65 statistically measures panum's area ranges of users under test, and acquires an average value of the panum's area ranges of the users under test having the same attribute. For example, the analyzing module 65 categories the users under test into males and females, statistically measuring panum's area ranges of the males and panum's area ranges of the females, and acquires an average value of the panum's area ranges of the males and females.

In another embodiment, upon acquiring the panum's area range of a user, the panum's area measurement apparatus, for example, the wearable display device, sends the panum's area range of the user to the interaction cloud, for example, the cloud server 91. In this embodiment, the cloud server 91 further includes the analyzing module 65. The analyzing module 65 statistically measures panum's area ranges of users under test having the same attribute as the user under test, and acquires an average value of the panum's area ranges. For example, the analyzing module 65 categories the users under test into the aged, the middle-aged and the children, statistically measures panum's area ranges of the aged and panum's are ranges of the adults, and acquires an average value of the panum's area ranges of the aged, the middle-aged and the children. Based on the panum's area ranges statistically measured according to the attributes of the users under test, an average value of the panum's area ranges of the users under test having different attributes, which provides technical reference data for preparing the three-dimensional content.

During adjustment, the user under test inputs an adjustment instruction by using the interaction end 70.

The adjusting module 63 adjusts the horizontal parallax amount towards a positive parallax amount based on the received adjustment instruction, and meanwhile the measuring module 64 acquires an in-screen parallax amount parameter $\Delta n_{ein}$ and determines an in-screen horizontal physical spacing $\Delta x_{in}$. In addition, the adjusting module 63 adjusts the horizontal parallax amount towards a negative parallax amount based on the received adjustment instruction, and meanwhile the measuring module 64 acquires an out-screen parallax amount parameter $\Delta n_{eout}$ and determines an out-screen horizontal physical spacing $\Delta x_{out}$. The measuring module 64 determines the panum's area range ($\mu_{in}$, $\mu_{out}$) based on the in-screen horizontal physical spacing $\Delta x_{in}$ and the out-screen horizontal physical spacing $\Delta x_{out}$.

A calculation process of the panum's area range is described in detail hereinafter.

Figure 4:
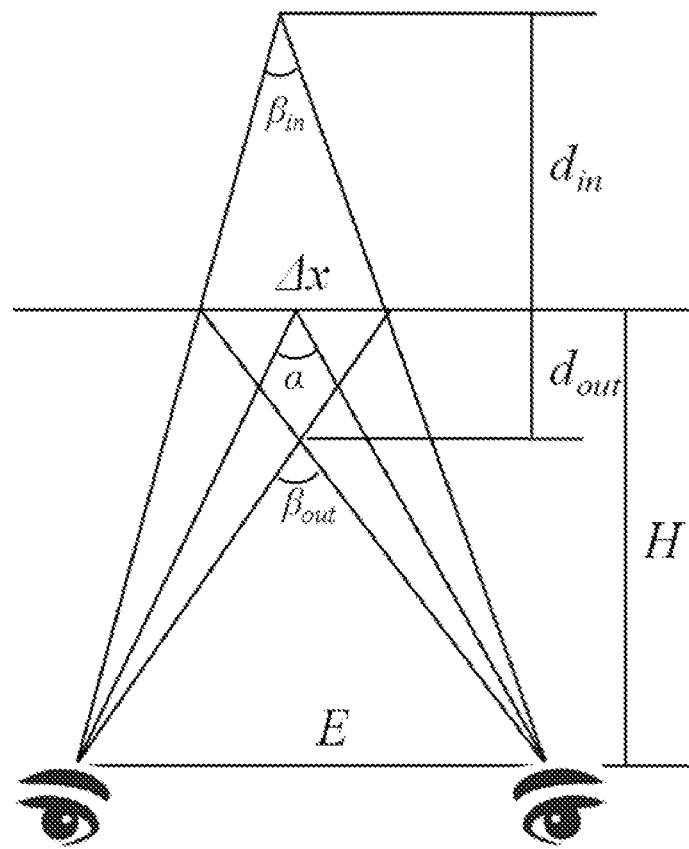
FIG. 4 is a schematic diagram of a binocular parallax principle of the panum's area measurement apparatus according to an embodiment of the present application.

In this embodiment, in the schematic diagram of a binocular parallax principle in FIG. 4, $\Delta_x$ denotes the horizontal physical spacing between the first homologous point A and the second homologous point B on the screen. Since the horizontal physical spacing $\Delta x$ between the homologous points is only related to a watching distance H, once the watching distance is determined, a physical spacing range between the left and right homologous points is determined, which is not related to the resolution, pixel size and viewing angle of the display screen.

In this embodiment of the present application, stereo parallax angles $\mu_{in}$ and $\mu_{out}$ are selected as evaluation parameters of the panum's area. As illustrated in FIG. 4, a parallax angle $\mu_{in}=\alpha-\beta_{in}$, and a negative parallax angle $\mu_{out}=\mu_{out}-\alpha$. Therefore, $\mu_{in}$ and $\mu_{out}$ denote two pieces of data to be measured. That is, $\mu_{in}$ and $\mu_{out}$ define a panum's area range. It should be noted that the panum's area range is a physiological category, which is related to the physiologic structure, different people have different panum's area ranges, and the panum's area range is not directly related to the display fashion, the screen size and the like. The panum's area measurement method in this embodiment eliminates the impacts caused by the device to the measurement data to the greatest extent, and more accurately reflects the stereo parallax angle range of the user, that is, the panum's area range.

Figure 5:
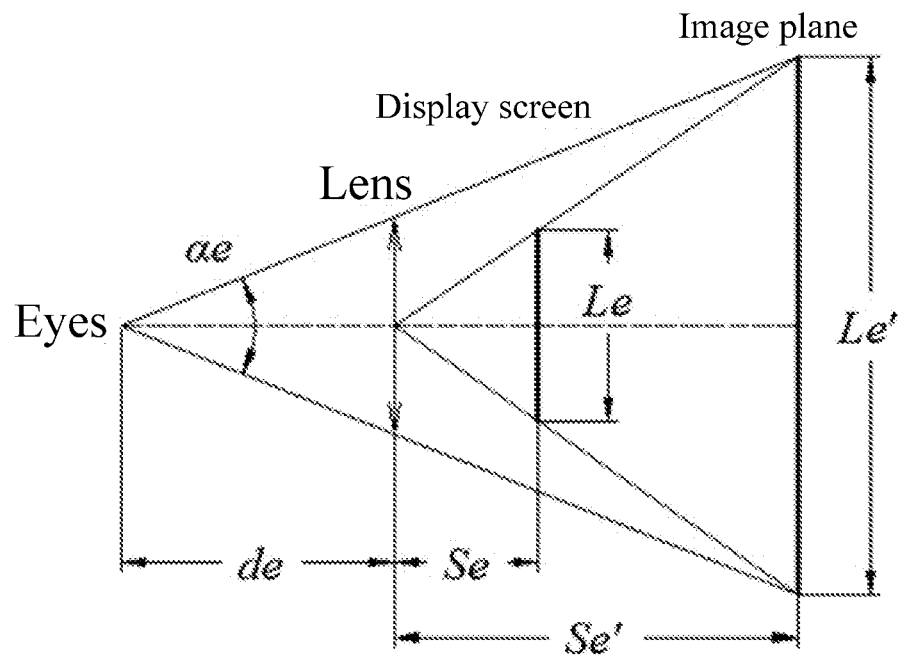
FIG. 5 is a monocular physical model diagram in a stereo display space in the panum's area measurement apparatus according to an embodiment of the present application.

FIG. 5 illustrates a monocular imaging physical model in a display space. The panum's area measurement apparatus in this embodiment, for example, the wearable display device, is configured with left and right optical display systems. These two monocular optical display systems have consistent parameters, and paralleled optical axes. A spacing between the optical axes is equal to a papillary distance E of the human eyes.

Each monocular optical display system may be equivalent to an ideal thin lens imaging system, and a two-dimensional display screen serves as an object plane. Human eyes see an upright image enlarged on the two-dimensional display screen, as illustrated in FIG. 5. Based on the geometric relationship, the following formulae may be obtained:

$$T_e = \frac{L'_e}{L_e} = \frac{S'_e}{S_e} \tag{1}$$

$$L'_e = 2(S'_e + d_e)\tan\left(\frac{\alpha_e}{2}\right) \tag{2}$$

$$L_e = M_e \xi_e \tag{3}$$

$$L'_e = M_e \xi'_e \tag{4}$$

$T_e$ denotes an object image magnification, $L_e$ denotes a horizontal physical size of an individual display screen, $L_e'$ denotes a horizontal physical size of an image on the individual display screen, $S_e$ denotes an object distance, that is, a distance from the display screen to the lens, and $S_e'$ denotes an image distance, which is generally a human eyes visibility distance of 25 cm. $\xi_e'$ denotes a pixel physical size of the image, $\xi_e$ denotes a pixel physical size on the plane of the display screen, $M_e$ denotes a horizontal resolution of the individual display screen, $d_e$ denotes a distance from the eyes to the center of the lens, and $\alpha_e$ denotes a horizontal viewing angle.

From formulae (2) and (4), it is known that the pixel size $\xi_e'$ on the image plane of the display screen is:

$$\xi'_e = \frac{2(S'_e + d_e)}{M_e}\tan\left(\frac{\alpha_e}{2}\right) \tag{5}$$

Figure 6:
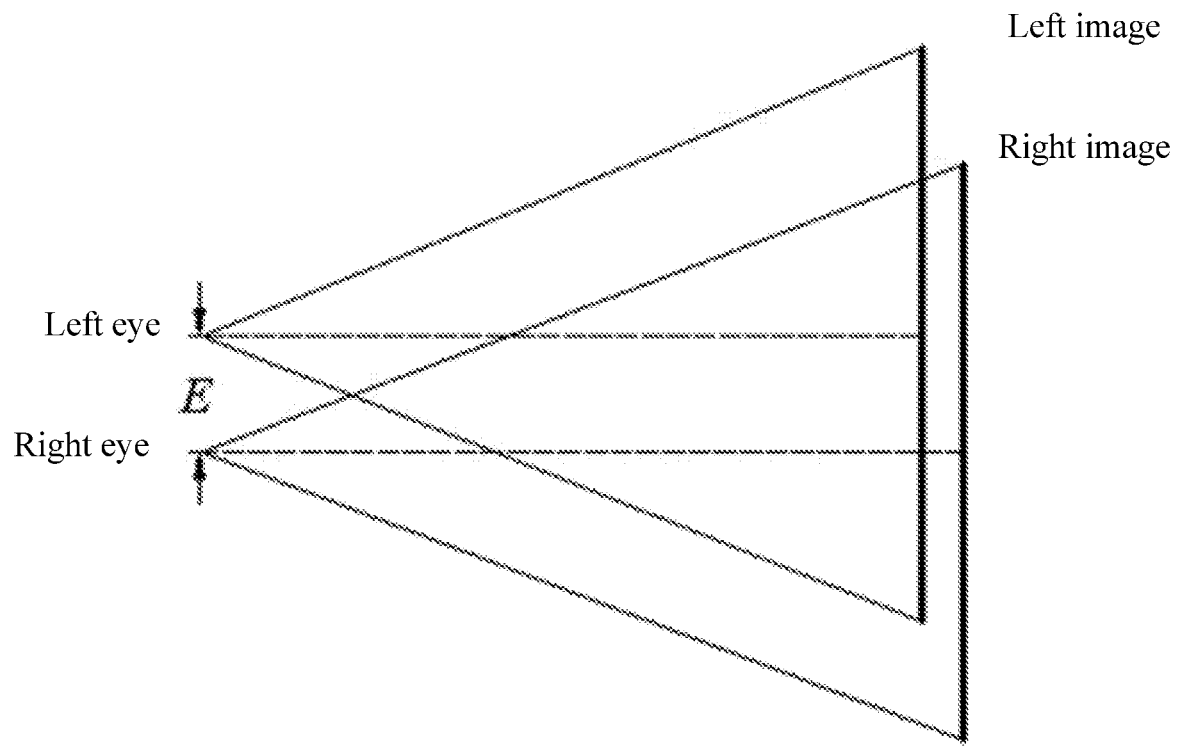
FIG. 6 is a binocular simplified model diagram of the panum's area measurement apparatus according to an embodiment of the present application.
Figure 7:
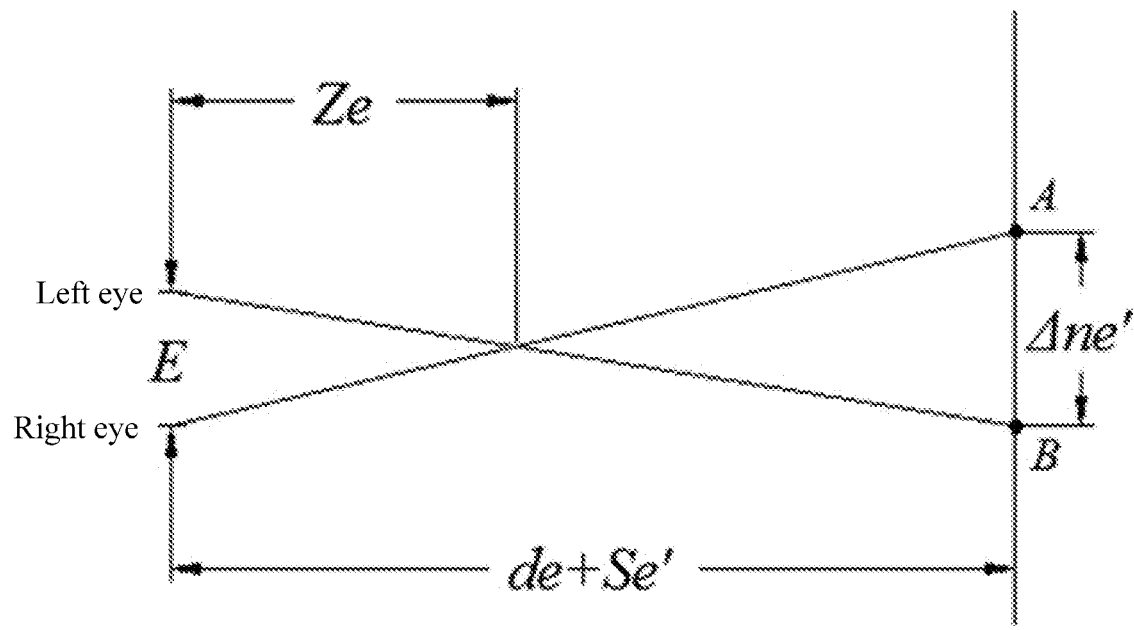
FIG. 7 is a binocular parallax model diagram of the panum's area measurement apparatus according to an embodiment of the present application.

As illustrated in FIG. 6, for ease of observation, the image planes on the left and right display screens are forward-and-backward shifted by a specific distance. In practice, the two image planes are in the same plane. In FIG. 6, the dotted lines are optical axes of two monocular optical display systems. FIG. 7 illustrates the scenario where the object goes out of the screen in the space where the first homologous point A and the second homologous point B are fused.

Based on the geometric relationships given in FIG. 6 and FIG. 7, a horizontal pixel spacing of a pair of homologous points, the first homologous point A and the second homologous point B, on the left and right display screens in the panum's area measurement apparatus, for example, the wearable display device, on the image plane is as follows:

$$\Delta n'_e = \Delta n_e + n_0 = \Delta n_e + \frac{E}{\xi'_e} \tag{6}$$

$\Delta n_e$ denotes a horizontal pixel spacing between the first homologous point A and the second homologous point B when the images on the left and right display screens totally coincide with each other, that is, the parallax amount parameter $\Delta n_e$. The parallax amount parameter $\Delta n_e$ includes the in-screen parallax amount parameter $\Delta n_{ein}$ and the out-screen parallax amount parameter $\Delta n_{eout}$.

When the user under test determines a critical position where double images appear based on the observation, the measuring module 64 introduces the in-screen parallax amount parameter $\Delta n_{ein}$ and the out-screen parallax amount parameter $\Delta n_{eout}$ to the formula, such that the horizontal physical spacing $\Delta x$ between the first homologous point A and the second homologous point B on the left and right display screens on the image plane of the wearable display device is obtained. The horizontal physical spacing $\Delta x$ includes the in-screen horizontal physical spacing $\Delta x_{in}$ and the out-screen horizontal physical spacing $\Delta x_{out}$, and the calculation formula thereof is as follows:

$$\Delta x = \Delta n_e \xi_e' + E \qquad (7)$$

The in-screen parallax amount parameter $\Delta n_{ein}$ and the out-screen parallax amount parameter $\Delta n_{eout}$ are introduced to formula (7), such that the in-screen horizontal physical spacing $\Delta x_{in}$ and the out-screen horizontal physical spacing $\Delta x_{out}$ are obtained.

Afterwards, based on the geometric relationship as illustrated in FIG. 4, the following formulae may be tenable:

1. With respect to an in-screen scenario where the parallax is positive:

$$\begin{cases} \alpha - \beta_{in} = \mu_{in} \\ \tan\left(\frac{\alpha}{2}\right) = \frac{E}{2H} \\ \tan\left(\frac{\beta_{in}}{2}\right) = \frac{E}{2(H+d_{in})} = \frac{\Delta x_{in}}{2d_{in}} \end{cases} \Rightarrow \begin{cases} \beta_{in} = 2\arctan\left(\frac{E}{2H}\right) - \frac{\mu_{in}\pi}{180} \\ \Delta x_{in} = E - 2H\tan\left(\frac{\beta_{in}}{2}\right) \end{cases} \qquad (8)$$

2. With respect to an out-screen scenario where the parallax is negative:

$$\begin{cases} \alpha - \beta_{out} = -\mu_{out} \\ \tan\left(\frac{\alpha}{2}\right) = \frac{E}{2H} \\ \tan\left(\frac{\beta_{out}}{2}\right) = \frac{E}{2(H-d_{out})} = \frac{\Delta x_{out}}{2d_{out}} \end{cases} \Rightarrow \begin{cases} \beta_{out} = 2\arctan\left(\frac{E}{2H}\right) + \frac{\mu_{out}\pi}{180} \\ \Delta x_{out} = 2H\tan\left(\frac{\beta_{out}}{2}\right) - E \end{cases} \qquad (9)$$

E denotes the papillary distance, which is generally 65 cm. H denotes the watching distance, that is, the distance from the human eyes to the screen, $d_{in}$ denotes an in-screen distance of a brain fused object, and $d_{out}$ denotes an out-screen distance thereof. $d_{in}$, $d_{out}$, $\beta_{in}$ and $\beta_{out}$ are offset in formula iterations, which are thus not described herein any further.

From formulae (8) and (9), it is known that a horizontal parallax physical size $\Delta x(H)$ is only a function of the watching distance H. Therefore, a horizontal parallax pixel distance between the first homologous point A and the second homologous point B is as follows:

$$\Delta n(H, \xi) = \frac{\Delta x(H)}{\xi} \qquad (10)$$

$\xi$ denotes a horizontal physical size of a pixel on the two-dimensional display screen.

Embodiment 2

This embodiment relates to a panum's area measurement method.

The horizontal pixel spacing between the first homologous point A and the second homologous point B is adjusted, for example, an in-screen parallax amount parameter $\Delta n_{ein}$ and an out-screen parallax parameter $\Delta n_{eout}$. During adjustment by using the interaction end 70, for example, increase and decrease of $\Delta n_e$ is controlled by leftward and rightward keys, the user under test wears a wearable display device, determines a critical position where no ghost appears, records the parallax amount parameter $\Delta n_e$ at this time, and calculates a panum's area range ($\mu_{in}$, $\mu_{out}$) of the user under test. A measuring module of the wearable display device removes a maximum value and a minimum value for all the parallax amount parameters, and takes an average value $\overline{\Delta n}_e$. Afterwards, $\overline{\Delta n}_e$ is introduced to formulae (5), (7), (8) and (9), such that two pieces of data $\mu_{in}$ and $\mu_{out}$ defining the panum's area range is obtained. The measurement result from the panum's area measurement method in this embodiment is not dependent on the device. With respect to any three-dimensional display device, the parallax amount parameter $\Delta n_e$ of three-dimensional content may be calculated based on system parameters and the panum's area measurement method. In addition, the three-dimensional content prepared based on this method maximally ensures senses of immersion and visual shock for the user on the premise of causing no sickness.

Figure 8:
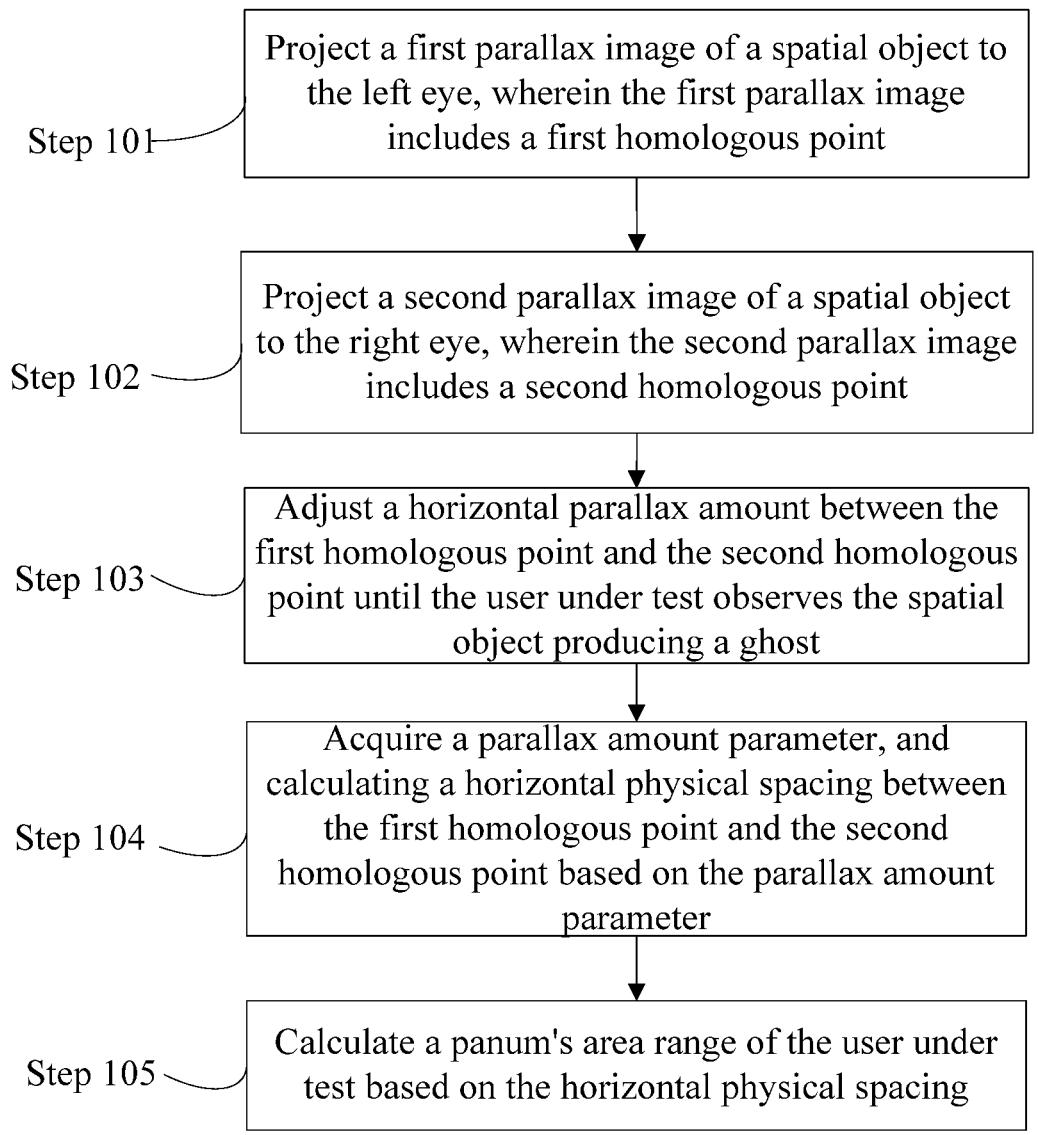
FIG. 8 is a schematic main flowchart of the panum's area measurement method according to an embodiment of the present application.

Referring to FIG. 8, from the perspective of panum's area measurement, the method mainly includes the following steps:

step 101: projecting a first parallax image of a spatial object to the left eye, wherein the first parallax image includes a first homologous point;

step 102: projecting a second parallax image of a spatial object to the right eye, wherein the second parallax image includes a second homologous point;

step 103: adjusting a horizontal parallax amount between the first homologous point and the second homologous point until the user under test observes the spatial object producing a ghost;

step 104: acquiring a parallax amount parameter $\Delta n_e$, and calculating a horizontal physical spacing $\Delta x$ between the first homologous point and the second homologous point based on the parallax amount parameter $\Delta n_e$; and step 105: calculating a panum's area range ($\mu_{in}$, $\mu_{out}$) of the user under test based on the horizontal physical spacing $\Delta x$.

Figure 9:
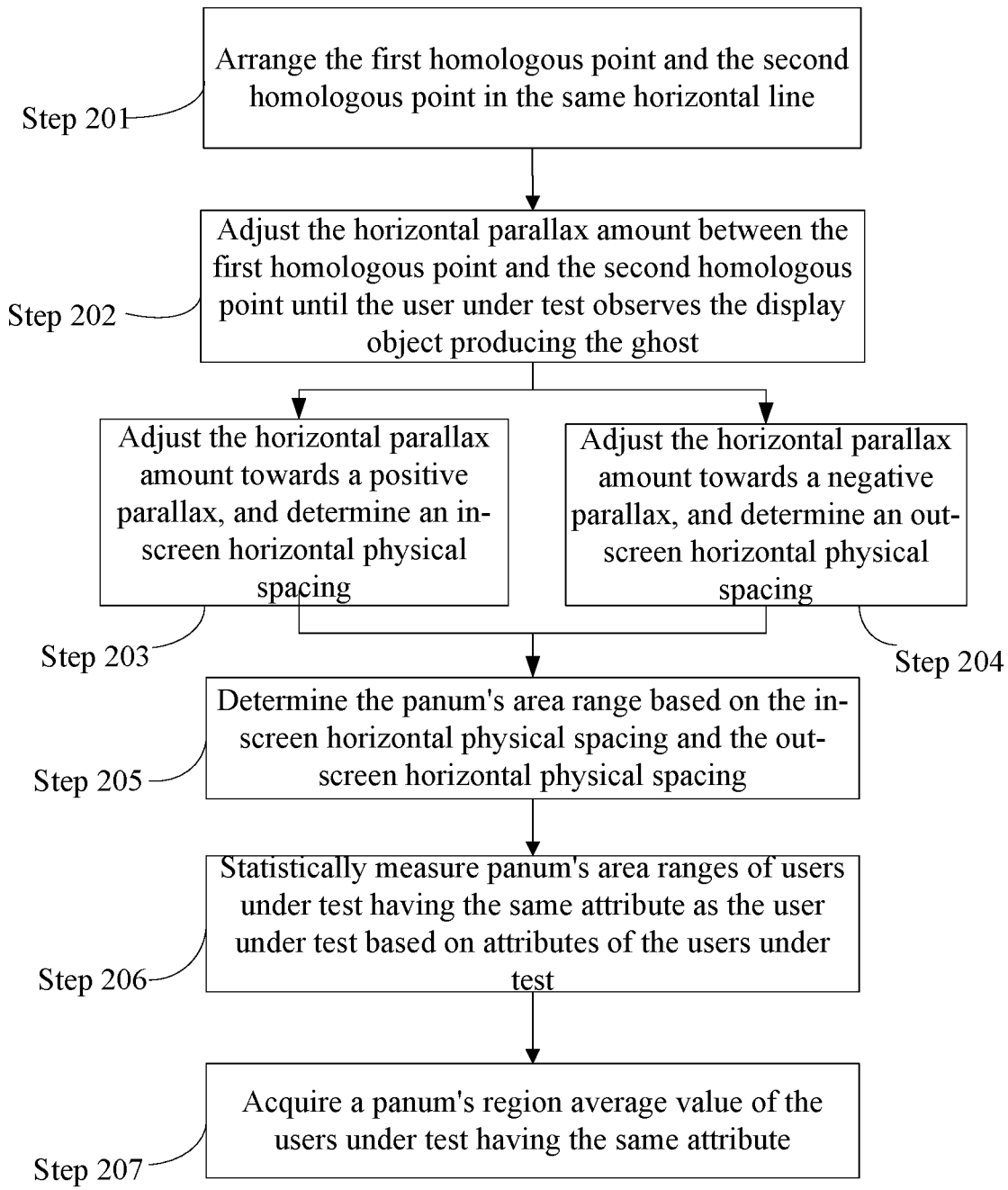
FIG. 9 is a schematic adjustment flowchart in the panum's area measurement method according to an embodiment of the present application.

Referring to FIG. 9, an adjustment flowchart in the panum's area measurement method is illustrated. The panum's area measurement method further includes:

step 201: arranging the first homologous point A and the second homologous point B in the same horizontal line;

step 202: adjusting the horizontal parallax amount between the first homologous point A and the second homologous point B until the user under test observes the display object producing the ghost;

step 203: adjusting the horizontal parallax amount towards a positive parallax, and determining an in-screen horizontal physical spacing;

step 204: adjusting the horizontal parallax amount towards a negative parallax, and determining an out-screen horizontal physical spacing;

step 205: determining the panum's area range based on the in-screen horizontal physical spacing and the out-screen horizontal physical spacing;

step 206: statistically measuring panum's area ranges of users under test having the same attribute as the user under test based on attributes of the users under test; and step 207: acquiring a panum's region average value of the users under test having the same attribute, and preparing three-dimensional display content based on the panum's area average value.

In the panum's area measurement method, the step of acquiring the parallax amount parameter $\Delta n_e$ includes:

adjusting the horizontal parallax amount towards a positive parallax amount, acquiring an in-screen parallax amount parameter $\Delta n_{ein}$, and determining an in-screen horizontal physical spacing $\Delta x_{in}$; adjusting the horizontal parallax amount towards a negative parallax amount, acquiring an out-screen parallax amount parameter $\Delta n_{eout}$, and determining an out-screen horizontal physical spacing $\Delta x_{out}$; and determining the panum's area range ($\mu_{in}$, $\mu_{out}$) based on the in-screen horizontal physical spacing $\Delta x_{in}$ and the out-screen horizontal physical spacing $\Delta x_{out}$.

The panum's area measurement apparatus is constituted by the wearable display device 60, the interaction end 70 and measurement software. The measurement software includes the adjusting module 63, the measuring module 64 and the analyzing module 65.

A specific measurement process is introduced as follows:

When the user under test wears the wearable display device, the measuring module 64 draws a first parallax image and a second parallax image, and the two parallax images are respectively displayed on two display screens of the wearable display device. The first parallax image and the second parallax image display the same spatial object. Only a distance difference in the horizontal direction is present between the spatial objects displayed in the first parallax image and the second parallax image, that is, only a horizontal parallax is present. No distance difference in the vertical direction is present therebetween, that is, no vertical parallax is present.

When the user under test sends an instruction for decreasing the parallax amount parameter via the interaction end, the adjusting module 63 may reduce the horizontal parallax between the spatial objects on the two parallax images based on a predetermined step, such that the horizontal parallax amount is adjusted towards a negative parallax.

When the user under test sends an instruction for increasing the parallax amount parameter via the interaction end, the adjusting module 63 may reduce the horizontal parallax between the spatial objects on the two parallax images based on a predetermined step, such that the horizontal parallax amount is adjusted towards a positive parallax.

When the horizontal parallax amount is changed from zero towards the negative parallax, the user may observe that left and right edges of the spatial object gradually create a ghost from a clear state. During transition from no ghost to appearance of a ghost, the corresponding parallax amount parameter $\Delta n_e$ is the out-screen parameter amount parameter $\Delta n_{eout}$. When the horizontal parallax amount is changed from zero towards the positive parallax, the user may likewise observe that the left and right edges of the spatial object gradually create a ghost from a clear state. During transition from no ghost to appearance of a ghost, the corresponding parallax amount parameter $\Delta n_e$ is the in-screen parallax amount parameter $\Delta n_{ein}$.

The measuring module 64 may introduce the acquired out-screen parameter amount parameter $\Delta n_{eout}$ and in-screen parallax amount parameter $\Delta n_{ein}$ to the following formula, such that the horizontal physical spacing $\Delta x$ between the first homologous point A and the second homologous point B on the left and right display screens on the image plane of the wearable display device is obtained.

$$\Delta x = \Delta n_e \xi_e' + E \qquad (7)$$

E denotes the pupillary distance of the human eyes, and the pixel size $\xi_e'$ of the display screen of the wearable display device on the image plane is as follows:

$$\xi_e' = \frac{2(S_e' + d_e)}{M_e} \tan\left(\frac{\alpha_e}{2}\right) \qquad (5)$$

$S_e'$ denotes an image distance which is generally a human eyes visibility distance of 25 cm, $d_e$ denotes a distance from the eyes to a center of a lens, $M_e$ denotes a horizontal resolution of an individual display screen in the display screen, and $\alpha_e$ denotes a horizontal viewing angle;

Afterwards, the horizontal physical spacing $\Delta x$ between the first homologous point A and the second homologous point B on the left and right display screens on the image plane of the wearable display device is introduced to the following formula, such that two values $\mu_{in}$ and $\mu_{in}$ defining the panum's area range of two eyes of the user is obtained.

$$\begin{cases} \beta_{in} = 2 \arctan\left(\frac{E}{2H}\right) - \frac{\mu_{in}\pi}{180} \\ \Delta x_{in} = E - 2H \tan\left(\frac{\beta_{in}}{2}\right) \end{cases} \qquad (8)$$

$$\begin{cases} \beta_{out} = 2 \arctan\left(\frac{E}{2H}\right) + \frac{\mu_{out}\pi}{180} \\ \Delta x_{out} = 2H \tan\left(\frac{\beta_{out}}{2}\right) - E \end{cases} \qquad (9)$$

In conclusion, with the panum's area measurement method and apparatus, and the wearable display device according to the embodiments of the present application, the measured panum's area range is only related to the horizontal parallax amount adjusted by the user at the interaction end, and with respect to different display measurement devices which employ the measurement method according to the present application, the panum's area measurement results remain unchanged, such that the panum's area range is accurately and standardly measured. According to the embodiments of the present application, by using the wearable display device, for example, a virtual reality apparatus or an augmented reality apparatus, independent image measurements are performed for left and right eyes by two optical systems and two display screens of the virtual reality apparatus or the augmented reality apparatus, which eliminates the interference caused between the left eye and the right eye. In addition, according to the embodiments of the present application, by dynamically controlling the horizontal parallax amount, for example, the distance, between the homologous points of the spatial object displayed in the first display unit and the second display unit, with respect to an individual user under test, this method may accurately measures the corresponding panum's area range. The panum's area range may be used for detection and prevention of eye diseases; or with respect to preparation of the three-dimensional content, statistical measurements may be performed for several users under test, and an average value of the panum's area ranges is acquired to improve comfortable experience in three-dimensional content preparation.

Embodiment 3

Figure 10:
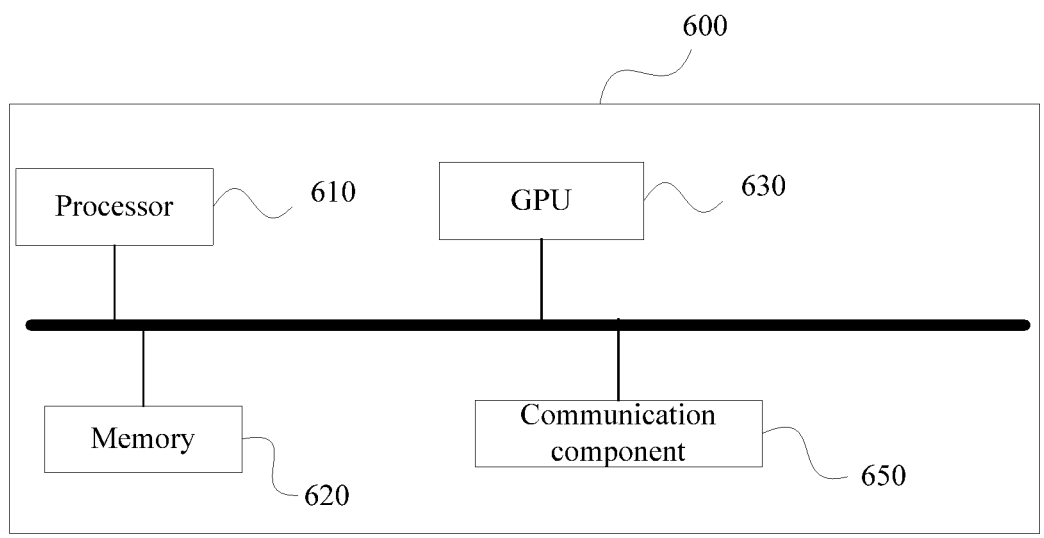
FIG. 10 is a schematic framework diagram of hardware for performing the panum's area measurement method according to an embodiment of the present application.

FIG. 10 is a schematic structural diagram of hardware of an electronic device 600 for performing the panum's area measurement method according to an embodiment of the present application.

As illustrated in FIG. 10, the electronic device 600 includes at least one processor 610, a memory and a communication component. FIG. 10 uses one processor 610 as an example. In an embodiment of a virtual reality wearable display device or an embodiment of an augmented reality wearable display device, the electronic device 600 may further include a graphics processing unit (GPU). The memory 620 stores instructions executable by the at least one processor 610. The instructions, when being executed by the at least one processor, may establish a data channel via the communication component 650, and cause the at least one processor to perform the panum's area measurement method.

The at least one processor 610, the memory 620 and the communication component 650 may be connected via a bus or in another manner, and FIG. 10 uses the bus as an example.

The memory 620, as a non-volatile computer readable storage medium, may be configured to store non-volatile software programs, and non-volatile computer-executable programs and modules, for example, the program instructions/modules (for example, the first display unit 61, the second display unit 62, the adjusting module 63, the measuring module 64, the analyzing module 65 and the connecting module 66 as illustrated in FIG. 2) corresponding to the panum's area measurement methods according to the embodiments of the present application. The non-volatile software programs, instructions and modules stored in the memory 620, when being run by the at least one processor 610, cause the processor 610 to perform various function applications and data processing of a wearable display device, that is, performing the panum's area measurement methods in the above method embodiments.

The memory 620 may include a program memory area and data memory area, wherein the program memory area may store operation systems and application programs needed by at least function; and the data memory area may store data created according to the usage of the wearable display device. In addition, the memory 620 may include a high speed random access memory, or include a non-volatile memory, for example, at least one disk storage device, a flash memory device, or another non-volatile solid storage device. In some embodiments, the memory 620 optionally includes the memory remotely arranged relative to the processor 610, and such remote memory may be connected to the electronic device over the network. Examples of the above network include, but not limited to, the Internet, Intranet, local area network, mobile communication network and a combination thereof.

One or more modules are stored in the memory 620, which, when being executed by the at least one processor 610, perform the panum's area measurement method according to any of the above method embodiments, for example, performing steps 101 to 105 in the method as illustrated in FIG. 8, steps 201 to 207 in the method as illustrated in FIG. 9; and implementing the functions of the first display unit 61, the second display unit 62, the adjusting module 63, the measuring module 64, the analyzing module 65 and the connecting module 66 as illustrated in FIG. 2.

The product may perform the method according to the embodiments of the present application, has corresponding function modules for performing the method, and achieves the corresponding beneficial effects. For technical details that are not illustrated in detail in this embodiment, reference may be made to the description of the methods according to the embodiments of the present application.

An embodiment of the present application provides a non-volatile computer-readable storage medium. The computer-readable storage medium stores computer-executable instructions, which, when being executed by at least one processor, cause the at least one processor to perform steps 101 to 105 in the method as illustrated in FIG. 8, steps 201 to 207 in the method as illustrated in FIG. 9; and implementing the functions of the first display unit 61, the second display unit 62, the adjusting module 63, the measuring module 64, the analyzing module 65 and the connecting module 66 as illustrated in FIG. 2.

The above described apparatus embodiments are merely for illustration purpose only. The units which are described as separate components may be physically separated or may be not physically separated, and the components which are illustrated as units may be or may not be physical units, that is, the components may be located in the same position or may be distributed into a plurality of network units. A part or all of the modules may be selected according to the actual needs to achieve the objectives of the technical solutions of the embodiments.

According to the above embodiments of the present application, a person skilled in the art may clearly understand that the embodiments of the present application may be implemented by means of hardware or by means of software plus a necessary general hardware platform. Persons of ordinary skill in the art may understand that all or part of the steps of the methods in the embodiments may be implemented by a program instructing relevant hardware. The program may be stored in a computer-readable storage medium and may be executed by at least one processor. When the program runs, the steps of the methods in the embodiments are performed. The storage medium may be any medium capable of storing program codes, such as read-only memory (ROM), a random access memory (RAM), a magnetic disk, or a compact disc-read only memory (CD-ROM).

Finally, it should be noted that the above embodiments are merely used to illustrate the technical solutions of the present application rather than limiting the technical solutions of the present application. Under the concept of the present application, the technical features of the above embodiments or other different embodiments may be combined, the steps therein may be performed in any sequence, and various variations may be derived in different aspects of the present application, which are not detailed herein for brevity of description. Although the present application is described in detail with reference to the above embodiments, persons of ordinary skill in the art should understand that they may still make modifications to the technical solutions described in the above embodiments, or make equivalent replacements to some of the technical features; however, such modifications or replacements do not cause the essence of the corresponding technical solutions to depart from the spirit and scope of the technical solutions of the embodiments of the present application.

What is claimed is:

1. A panum's area measurement method, comprising:
projecting a first parallax image of a spatial object to the left eye of a user under test, and projecting a second parallax image of a spatial object to the right eye of the user under test, the first parallax image comprising a first homologous point and the second parallax image comprising a second homologous point;
adjusting a horizontal parallax amount between the first homologous point and the second homologous point until the user under test observes the spatial object producing a ghost, acquiring a parallax amount parameter $\Delta n_e$, and calculating a horizontal physical spacing $\Delta x$ between the first homologous point and the second homologous point based on the parallax amount parameter $\Delta n_e$; and
calculating a panum's area range ($\mu_{in}$, $\mu_{out}$) of the user under test based on the horizontal physical spacing $\Delta x$;

wherein the acquiring a parallax amount parameter $\Delta n_e$ comprises:

adjusting the horizontal parallax amount towards a positive parallax amount, acquiring an in-screen parallax amount parameter $\Delta n_{ein}$, and determining an in-screen horizontal physical spacing $\Delta x_{in}$; adjusting the horizontal parallax amount towards a negative parallax amount, acquiring an out-screen parallax amount parameter $\Delta n_{eout}$, and determining an out-screen horizontal physical spacing $\Delta x_{out}$; and determining the panum's area range ($\mu_{in}$, $\mu_{out}$) based on the in-screen horizontal physical spacing $\Delta x_{in}$ and the out-screen horizontal physical spacing $\Delta x_{out}$.

2. The method according to claim 1, further comprising:
statistically measuring panum's area ranges of users under test having the same attribute as the user under test based on attributes of the users under test, and acquiring a panum's region average value of the users under test having the same attribute; and preparing three-dimensional display content based on the panum's area average value.

3. The method according to claim 1, wherein the horizontal physical spacing $\Delta x$ comprises the in-screen physical spacing $\Delta x_{in}$ and the out-screen horizontal physical spacing $\Delta x_{out}$, which are calculated by the following formula:

$$\Delta x = \Delta n_e \xi_e' + E \quad (7)$$

wherein E denotes a pupillary distance of the user under test, and $\xi_e'$ denotes a pixel size of a display screen on an image plane;

$$\xi_e' = \frac{2(S_e' + d_e)}{M_e} \tan\left(\frac{\alpha_e}{2}\right) \quad (5)$$

wherein $S_e'$ denotes an image distance which is generally a human eyes visibility distance of 25 cm, $d_e$ denotes a distance from the eyes to a center of a lens, $M_e$ denotes a horizontal resolution of an individual display screen in the display screen, and $\alpha_e$ denotes a horizontal viewing angle;

wherein a critical value of the panum's area range ($\mu_{in}$, $\mu_{out}$) is as follows:

$$\begin{cases} \beta_{in} = 2 \arctan\left(\frac{E}{2H}\right) - \frac{\mu_{in}\pi}{180} \\ \Delta x_{in} = E - 2H \tan\left(\frac{\beta_{in}}{2}\right) \end{cases} \quad (8)$$

$$\begin{cases} \beta_{out} = 2 \arctan\left(\frac{E}{2H}\right) + \frac{\mu_{out}\pi}{180} \\ \Delta x_{out} = 2H \tan\left(\frac{\beta_{out}}{2}\right) - E \end{cases} \quad (9)$$

wherein E denotes the pupillary distance of the user under test, and H denotes a watching distance.

4. The method according to claim 1, further comprising:
sending the panum's area range ($\mu_{in}$, $\mu_{out}$) to a cloud server.

5. A wearable display device, comprising a first display unit and a second display unit, wherein
the wearable display device further comprises an adjusting module and a measuring module that receive a signal from the interaction end; wherein
the first display unit is configured to project a first parallax image of a spatial object to the left eye of a user under test, and the second display unit is configured to project a second parallax image of the spatial object to the right eye of the user under test, the first parallax image comprising a first homologous point and the second parallax image comprising a second homologous point;

the adjusting module is configured to adjust, under control of the interaction end, a horizontal parallax amount between the first homologous point and the second homologous point until the user under test observes the spatial object producing a ghost; and the measuring module is configured to acquiring a parallax amount parameter $\Delta n_e$, calculate a horizontal physical spacing $\Delta_x$ between the first homologous point and the second homologous point based on the parallax amount parameter $\Delta n_e$, and calculate a panum's area range ($\mu_{in}$, $\mu_{out}$) of the user under test based on the horizontal physical spacing $\Delta x$;

wherein the adjusting module is further configured to adjust the horizontal parallax amount towards a positive parallax amount, and the measuring module is further configured to acquire an in-scree parallax amount parameter $\Delta n_{ein}$, and determine an in-screen horizontal physical spacing $\Delta x_{in}$;

the adjusting module is further configured to adjust the horizontal parallax amount towards a negative parallax amount, and the measuring module is further configured to acquire an out-screen parallax amount parameter $\Delta n_{eout}$, and determine an out-screen horizontal physical spacing $\Delta x_{out}$; and the measuring module is further configured to determine the panum's area range ($\mu_{in}$, $\mu_{out}$) base on the in-screen horizontal physical spacing $\Delta x_{in}$ and the out-screen horizontal physical spacing $\Delta x_{out}$.

6. The wearable display device according to claim 5, further comprising:
an analyzing module, which is configured to statistically measure panum's area ranges of users under test having the same attribute as the user under test, and acquire a panum's region average value of the users under test having the same attribute.

7. The wearable display device according to claim 5, wherein the horizontal physical spacing $\Delta x$ comprising the in-screen physical spacing $\Delta x$ in and the out-screen horizontal physical spacing $\Delta x$ out which are calculated by the following formula:

$$\Delta x = \Delta n_e \xi_e' + E \quad (7)$$

wherein E denotes a pupillary distance of the user under test, and $\xi_e'$ denotes a pixel size of a display screen on an image plane;

$$\xi_e' = \frac{2(S_e' + d_e)}{M_e} \tan\left(\frac{\alpha_e}{2}\right) \quad (5)$$

wherein $S_e'$ denotes an image distance which is generally a human eyes visibility distance of 25 cm, $d_e$ denotes a distance from the eyes to a center of a lens, $M_e$ denotes a horizontal resolution of an individual display screen in the display screen, and $\alpha_e$ denotes a horizontal viewing angle;

wherein a critical value of the panum's area range ($\mu_{in}$, $\mu_{out}$) is as follows:

$$\begin{cases} \beta_{in} = 2 \arctan\left(\frac{E}{2H}\right) - \frac{\mu_{in}\pi}{180} \\ \Delta x_{in} = E - 2H \tan\left(\frac{\beta_{in}}{2}\right) \end{cases} \quad (8)$$

-continued $$\begin{cases} \beta_{out} = 2\arctan\left(\dfrac{E}{2H}\right) + \dfrac{\mu_{out}\pi}{180} \\ \Delta x_{out} = 2H\tan\left(\dfrac{\beta_{out}}{2}\right) - E \end{cases} \quad (9)$$

wherein E denotes the pupillary distance of the user under test, and H denotes a watching distance.

8. The wearable display device according to claim 5, wherein the wearable display device is connected to a cloud server, and the wearable display device comprises a sending module, which is configured to send the panum's area range ($\mu_{in}$, $\mu_{out}$) to the cloud server.

9. The wearable display device according to claim 8, wherein the interaction end comprises a head posture acquisition apparatus; wherein the head posture acquisition apparatus is configured to acquire a head posture parameter of the user under test and adjust the parallax amount parameter $\Delta n_e$.

10. The wearable display device according to claim 9, wherein the wearable display device is a virtual reality device or an augmented reality device.

11. An electronic device, comprising:
  at least one processor; and
  a memory and a communication component that are communicably connected to the at least one processor; wherein
  the memory stores instructions executable by the at least one processor, wherein, the instructions, when being executed by the at least one processor, cause the at least one processor to establish a data channel by using the communication component, such that the at least one processor perform the steps of:
  projecting a first parallax image of a spatial object to the left eye of a user under test, and projecting a second parallax image of a spatial object the right eye of the user under test, the first parallax image comprising a first homologous point and the second parallax image comprising a second homologous point;
  adjusting a horizontal parallax amount between the first homologous point and the second homologous point until the user under test observes the spatial object producing a ghost acquiring a parallax amount parameter $\Delta n_e$, and calculating a horizontal physical spacing $\Delta x$ between the first homologous point and the second homologous point based on the parallax amount parameter $\Delta n_e$; and
  calculating a panum s area range ($\mu_{in}$, $\mu_{out}$) of the user under test based on the horizontal physical spacing $\Delta x$;
  wherein the acquiring a parallax amount parameter $\Delta n_e$ comprises:
  adjusting the horizontal parallax amount towards a positive parallax amount, acquiring an in-screen parallax amount parameter $\Delta n_{ein}$, and determining an in-screen horizontal physical spacing $\Delta x_{in}$; adjusting the horizontal parallax amount towards a negative parallax amount, acquiring an out-screen parallax amount parameter $\Delta n_{eout}$, and determining an out-screen horizontal physical spacing $\Delta x_{out}$; and determining the panum's area range ($\mu_{in}$, $\mu_{out}$) based on the in-screen horizontal physical spacing $\Delta x_{in}$ and the out-screen horizontal physical spacing $\Delta x_{out}$.

12. The electronic device according to claim 11, further comprising: statistically measuring panum's area ranges of users under test having the same attribute as the user under test based on attributes of the users under test, and acquiring a panum's region average value of the users under test having the same attribute; and
  preparing three-dimensional display content based on the panum's area average value.

13. The electronic device according to claim 11, wherein the horizontal physical spacing $\Delta x$ comprises the in-screen physical spacing $\Delta x_{in}$ and the out-screen horizontal physical spacing $\Delta x_{out}$, which are calculated by the following formula:

$$\Delta x = \Delta n_e \xi_e' + E \quad (7)$$

wherein E denotes a pupillary distance of the user under test, and $\xi_e'$ denotes a pixel size of a display screen on an image plane;

$$\xi_e' = \dfrac{2(S_e' + d_e)}{M_e}\tan\left(\dfrac{\alpha_e}{2}\right) \quad (5)$$

wherein $S_e'$ denotes an image distance which is generally a human eyes visibility distance of 25 cm, $d_e$ denotes a distance from the eyes to a center of a lens, $M_e$ denotes a horizontal resolution of an individual display screen in the display screen, and $\alpha_e$ denotes a horizontal viewing angle;
wherein a critical value of the panum's area range ($\mu_{in}$, $\mu_{out}$) is as follows:

$$\begin{cases} \beta_{in} = 2\arctan\left(\dfrac{E}{2H}\right) - \dfrac{\mu_{in}\pi}{180} \\ \Delta x_{in} = E - 2H\tan\left(\dfrac{\beta_{in}}{2}\right) \end{cases} \quad (8)$$

$$\begin{cases} \beta_{out} = 2\arctan\left(\dfrac{E}{2H}\right) + \dfrac{\mu_{out}\pi}{180} \\ \Delta x_{out} = 2H\tan\left(\dfrac{\beta_{out}}{2}\right) - E \end{cases} \quad (9)$$

wherein E denotes the pupillary distance of the user under test, and H denotes a watching distance.

14. The electronic device according to claim 11, further comprising: sending the panum's area range ($\mu_{in}$, $\mu_{out}$) to a cloud server.

* * * * *